United States Patent
Vaara et al.

(10) Patent No.: US 9,763,996 B2
(45) Date of Patent: Sep. 19, 2017

(54) POLYMYXIN DERIVATIVE AND USES THEREOF

(71) Applicant: Northern Antibiotics Ltd., Helsinki (FI)

(72) Inventors: Martti Sakari Vaara, Espoo (FI); Timo Ilmari Vaara, Helsinki (FI)

(73) Assignee: Northern Antibiotics, Ltd., Espoo (FI)

( * ) Notice: Subject to any disclaimer, the term of this patent is extended or adjusted under 35 U.S.C. 154(b) by 0 days.

(21) Appl. No.: 15/000,443

(22) Filed: Jan. 19, 2016

(65) Prior Publication Data

US 2016/0206684 A1    Jul. 21, 2016

Related U.S. Application Data

(60) Provisional application No. 62/104,448, filed on Jan. 16, 2015, provisional application No. 62/181,005, filed on Jun. 17, 2015.

(51) Int. Cl.
*A61K 38/12* (2006.01)
*C07K 7/62* (2006.01)
*A61K 45/06* (2006.01)
*A61K 38/00* (2006.01)

(52) U.S. Cl.
CPC .............. *A61K 38/12* (2013.01); *A61K 45/06* (2013.01); *C07K 7/62* (2013.01); *A61K 38/00* (2013.01)

(58) Field of Classification Search
CPC .................. A61K 38/12; C07K 7/62
See application file for complete search history.

(56) References Cited

U.S. PATENT DOCUMENTS 7,807,637 B2    10/2010   Vaara et al.
2006/0004185 A1    1/2006   Leese et al.

FOREIGN PATENT DOCUMENTS

WO    2008/017734 A1    2/2008
WO    2013/072695 A1    5/2013
WO    2014/188178 A1    11/2014

OTHER PUBLICATIONS

Burt et al. (Oct. 16, 2013) "Application of emerging biomarkers of acute kidney injury in development of kidney-sparing polypeptide-based antibiotics," Drug Chem. Toxicol. 37:204-212.
Keirstead (Nov. 4, 2013) "Early prediction of polymyxin-induced nephrotoxicity with next-generation urinary kidney injury biomarkers," Toxicol. Sci. 137:278-291.
Magee et al. (Jun. 18, 2013) "Discovery of Dap-3 polymyxin analogues for the treatment of multidrug-resistant Gram-negative nosocomial infections," J. Med. Chem. 56:5079-5093.
Mingeot-Leclercq et al. (2012) "Novel polymyxin derivatives are less cytotoxic than polymyxin B to renal proximal tubular cells," Peptides. 35:248-252.
Quale et al. (Dec. 23, 2011) "Activity of polymyxin B and the novel polymyxin analogue CB-182,804 against contemporary Gram-negative pathogens in New York City," Microb. Drug Resist. 18(2):132-136.
Vaara et al. (Feb. 13, 2013) "Novel derivatives of polymyxins," J. Antimicrob. Chemother. 68:1213-1219.
Vaara et al. (Nov. 20, 2012) "The novel polymyxin derivative NAB739 is remarkably less cytotoxic than polymyxin B and colistin to human kidney proximal tubular cells," Int. J. Antimicrob. Chemother. 41:292-293.
Vaara et al. (2010) "Polymyxins and their novel derivatives," Curr. Opin. Microbiol. 13(5):574-581.
Vaara et al. (2010) "Structure-activity studies on novel polymyxin derivatives that carry only three positive charges," Peptides, 31:2318-2321.
Vaara et al. (2008) "Novel polymyxin derivatives carrying only three positive charges are effective antibacterial agents," J. Antimicrob. Chemother. 52:3229-3236.
Kazawa et al. (Jan. 9, 2009) "Contribution of Each Amino Acid Residue in Polymyxin B3 to Antimicrobial and Lipopolysaccharide Binding Activity," Chem. Pharm. Bull. 57(3):240-244.

*Primary Examiner* — Christina Bradley
(74) *Attorney, Agent, or Firm* — Lathrop Gage LLP; Sean M. Coughlin, Esq.

(57) ABSTRACT

The present invention relates to a polymyxin derivative of formula (I)

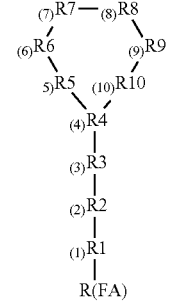

wherein
R1 is Dab
R2 is Thr
R3 is DThr
R4 is Dab
R5 is Dab
R6 is DPhe
R7 is Leu
R8 is Abu
R9 is Dab;
R10 is Thr; and
R(FA) is octanoyl;
and pharmaceutically acceptable salts thereof. The invention further relates to their use in the treatment of infections caused by Gram-negative bacteria.

12 Claims, 4 Drawing Sheets

POLYMYXIN DERIVATIVE AND USES THEREOF

CROSS-REFERENCE TO RELATED APPLICATIONS

This application claims priority to U.S. Provisional Patent Application No. 62/104,448 filed Jan. 16, 2015 and U.S. Provisional Patent Application No. 62/181,005 filed Jun. 17, 2015, the contents of which are incorporated by reference herein.

FIELD OF THE INVENTION

The present invention relates to polymyxin derivatives and to uses thereof in the treatment of infections caused by Gram-negative bacteria.

BACKGROUND OF THE INVENTION

Septic infections kill more than 215,000 Americans each year. It is estimated that 750,000 Americans are infected with severe sepsis and 29% of them die from it each year. Sepsis deaths comprise 9% of all death cases in the U.S. Sepsis kills as many Americans as myocardial infarctions, even more than traffic accidents.

Two to three million Americans acquire a hospital infection each year and 10% of these infections progress to sepsis. More than 90,000 of these patients die from sepsis infected in hospitals.

*Escherichia coli* and *Klebsiella pneumoniae*, both Gram-negative bacteria, cause almost 40% of all community-acquired septic infections and approximately one-third of all healthcare-associated septic infections. Out of all Gram-negative septic infections, they cause approximately 60-75%. Other Gram-negative causative agents of septic infections include *Acinetobacter baumannii* and *Pseudomonas aeruginosa*. Altogether, Gram-negative bacteria cause more than 40% of all septic infections, and many of these bacteria are extremely multiresistant.

Polymyxins are a group of closely related antibiotic substances produced by strains of *Paenibacillus polymyxa* and related organisms. These cationic drugs are relatively simple peptides with molecular weights of about 1000. Polymyxins, such as polymyxin B, are decapeptide antibiotics, i.e. they are made of ten (10) aminoacyl residues. They are bactericidal and especially effective against Gram-negative bacteria such as *E. coli* and other species of Enterobacteriaceae, *Pseudomonas, A. baumannii*, and others. However, polymyxins have severe adverse effects, including nephrotoxicity and neurotoxicity. These drugs thus have limited use as therapeutic agents because of high systemic toxicity.

The pandemic of extremely multiresistant Gram-negative bacteria has now forced clinicians to reinstate polymyxins as the last-line therapy of severe infections, even though polymyxins are notoriously nephrotoxic. The nephrotoxicity of polymyxins may complicate the therapy or may even require its discontinuation. Accordingly, the risk of nephrotoxicity must be weighed against the beneficial effects on patient survival. According to recent studies, the nephrotoxicity rate of polymyxin B and colistin (liberated from colistin methanesulphonate) varies from 10% to 30%, but in selected materials the rate for colistin may be as high as 43 to 48% and that for polymyxin B as high as 55%. Accordingly, individual variation is high (Vaara, M. 2013, New derivatives of polymyxins, Journal of Antimicrobial Chemotherapy 2013, 68: 1213-9). The situation is made even more unfortunate by contemporary data indicating that in critically ill patients the current dosage regimens are suboptimal and lead to too low serum concentrations. Clinicians are thus advised to use larger doses, but this further increases nephrotoxicity.

SUMMARY OF THE INVENTION

It is thus an object of the present invention to provide a polymyxin derivative effective against Gram-negative bacteria and having reduced nephrotoxicity. The objects of the invention are achieved by a polymyxin derivative and pharmaceutically acceptable salts thereof and by uses thereof which are characterized by what is stated in the independent claims. The preferred embodiments of the invention are disclosed in the dependent claims.

BRIEF DESCRIPTION OF THE DRAWINGS

In the following the invention will be described in greater detail by means of preferred embodiments with reference to the attached [accompanying] drawings, in which.

DETAILED DESCRIPTION OF THE INVENTION

Figure 1:
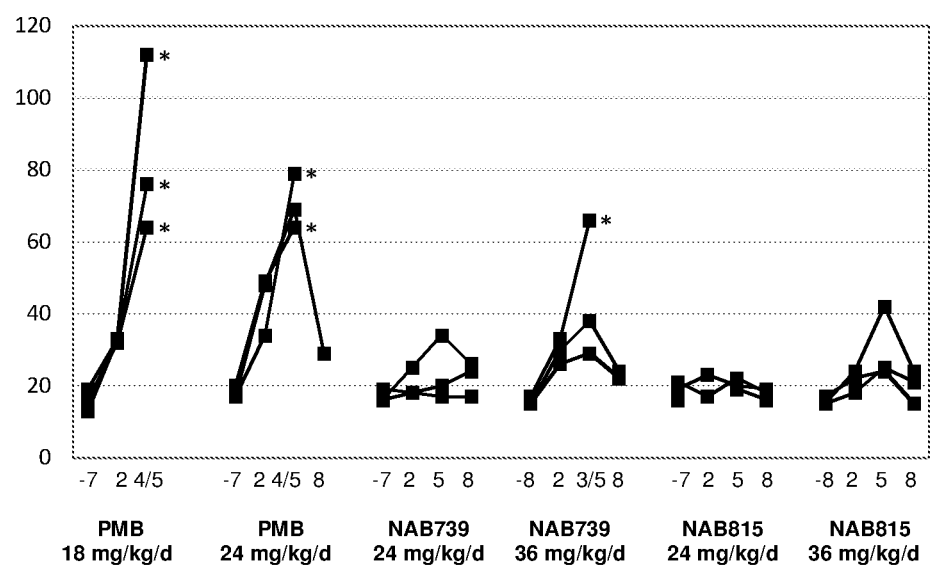
FIG. 1 shows S-BUN (mg/dL) before (day −7/−8) and during (days 2-8) treatment with polymyxin B (PMB), NAB739, or NAB815 (3 animals per group, IV, TID)

Recently, several attempts have been made to develop better tolerated derivatives of polymyxins. We have earlier shown that compounds disclosed in PCT/FI2007/050441 (the entire contents and disclosures of which are hereby incorporated by reference) have remarkable antibacterial activity and are useful in treating infections caused by Gram-negative bacteria. Furthermore, we have suggested that these compounds, all carrying three (3) positive charges only, are less nephrotoxic than compounds that carry five (5) positive charges, and we have also shown preliminary evidence for it (Vaara M. et al. Novel polymyxin derivatives carrying only three positive charges are effective antibacterial agents. Antimicrob Agents Chemother 2008, 52: 3229-36; Vaara M. and Vaara T. Polymyxin derivatives and uses thereof. 2010. U.S. Pat. No. 7,807,637; Vaara M. Polymyxins and their novel derivatives. Curr Opin Microbiol 2010; 13: 574-81; Mingeot-Leclercq M.-P. Novel polymyxin derivatives are less cytotoxic than polymyxin B to renal proximal tubular cells. Peptides 2012; 35: 248-52; Vaara M. and Vaara T. The novel polymyxin derivative NAB739 is remarkably less cytotoxic than polymyxin B and colistin to human kidney proximal tubular cells. Int J Antimicrob Chemother 2013, 41:292-3; Vaara, M. 2013, New derivatives of polymyxins, Journal of Antimicrobial Chemotherapy 2013, 68: 1213-9).

While these compounds, such as NAB739, have good antibacterial activity against Gram-negative bacteria, it is desirable to try to develop derivatives that are still better tolerated in a reliable and unequivocal fashion.

Now, it was surprisingly realized that a specific polymyxin derivative as defined herein displays wanted high antibacterial effect against Gram-negative bacteria without unacceptable nephrotoxicity.

The development of CB-182,804, a molecule otherwise identical to polymyxin B, but carrying 2-chloro-phenylamino-carbonyl as the fatty acyl moiety linked to the N-terminus, under the U.S. Patent Application 2006004185 (see also Quale J. et al., Activity of polymyxin B and the novel polymyxin analogue CB-182,804 against contemporary Gram-negative pathogens in New York City, Microb Drug Resist 2012, 13: 574-81) was discontinued in 2010. A Dap-3 polymyxin analogue did not differ sufficiently from polymyxin B in the nephrotoxicity studies in dogs (Magee T. V. et al., Discovery of Dap-3 Polymyxin Analogues for the Treatment of Multidrug-Resistant Gram-Negative Nosocomial Infections, J. Med. Chem. 2013, 56: 5079-5093). Both programs included only compounds with five positive charges. The attempts also include that by Kern and coworkers (Keirstead N, Early prediction of polymyxin-induced nephrotoxicity with next generation urinary kidney injury biomarkers, Toxicol Sci 2014, 137: 278-91); no details or any further progress have been published.

Patent application WO/2013/072695 describes more than 30 polymyxin nonapeptides, each carrying at least four positive charges. Several of them were less cytotoxic than polymyxin B and colistin to human renal proximal tubule epithelial cell (hRPTEC) line HK-2. Furthermore, in a 7-day rat study, three of them increased urinary cystatin C, albumin and NAG levels to a lesser extent than equivalent dose of colistin.

Patent application WO/2014/188178 continues the work described in WO/2013/072695. As the title "polymyxin derivatives and their use in combination therapy together with different antibiotics" indicates, the main emphasis is potentiation of the activity of other antibiotics such as rifampin by the polymyxin derivatives of the earlier patent application as well as of several novel derivatives. Some of the novel derivatives (example derivatives 44, 46 and 48) carry DSer at R3 (numbering of the amino acyl residues according to the scheme commonly used for polymyxins, i.e., the first residue from the N-terminal of polymyxin B is numbered as R1). One of them (derivative 46) carries three positive charges only. It is an NAB739 analogue, otherwise identical to it but carries as the terminal moiety 2-cyclohexyl-2-hydroxyethanoyl (also known as 2-cyclohexyl-2-hydroxyacetyl) whereas NAB739 carries octanoyl. Altogether, the application describes some 100 derivatives, which, with the exception of the derivative example 46 described above, carry 4-6 positive charges. All the derivatives had their cyclic heptapeptide part identical to polymyxin B, with the exception of derivative examples 19, 30, 31, and 32 that had their cyclic heptapeptide part identical to that of polymyxin E and the derivative example 50 that had its cyclic heptapeptide part is identical to that of polymyxin S. Many of the derivatives were less cytotoxic than polymyxin B and colistin to human renal proximal tubule epithelial cell (hRPTEC) line HK-2. Furthermore, in a 7-day rat study, three of them (example derivatives 1, 4 and 10) were shown to increase urinary cystatin C, albumin and NAG levels to a lesser extent than equivalent dose of colistin. In the application it is suggested, that the presence of an amino functionality within the N-terminal group may reduce nephrotoxicity. However, in the notoriously nephrotoxic polymyxin B and colistin, R1 does carry a free amino group. The application also suggests that a hydroxyl group and/or a heterocyclyl group in the N-terminus may have a similar toxicity-reducing effect.

Finding a clinically relevant nephrotoxicity model is challenging. Magee T. V. et al., 2013 (see above) showed that a polymyxin derivative 5x, where R3 is diaminopropionyl (instead of diaminobutyryl) and a relatively polar 6-oxo-1-phenyl-1,6-dihydropyridine-3-carbonyl as a fatty acyl replacement, was significantly less cytotoxic to human renal proximal tubule epithelial cells (hRPTEC) than polymyxin B. Furthermore, in a 7-day rat study 5x was less nephrotoxic than polymyxin B. Encouraged by these results, the authors conducted a 7-day dog study. In this study, the nephrotoxicity results were only slightly in favor of 5x. The authors concluded that 5x was better tolerated than polymyxin B in rat with respect to renal lesions but that this advantage collapsed in the dog, pointing to the failure of the hRPTEC assay to predict for nephrotoxicity in that species.

In another study from the same laboratory (Burt D. et al. Application of emerging biomarkers of acute kidney injury in development of kidney-sparing polypeptide-based antibiotics. Drug Chem Toxicol. 2014; 37:204-12), polymyxin B elicited a rapid onset of S-Crea and BUN response in dogs and monkeys but not in rats. The authors concluded that the lack of response in rats might be attributed to species-specific polymyxin B responses and differences in kidney physiology. Compound 5x was not included in this study. Because S-Crea and BUN are very relevant markers of nephrotoxicity in clinical therapy, an animal model such as dog or monkey could be expected to be much more reliable than rodent models to predict nephrotoxicity in humans.

Thus the in vitro hRPTEC assay and in vivo rat studies, as attractive as they otherwise are, may misleadingly give promising results that cannot be duplicated in animal models closer to human.

NAB815 and its previously described reference compound NAB739 fall into the category of polymyxins that carry three (3) positive charges only. As shown now here, both are clearly less nephrotoxic than polymyxin B in cynomolgus monkeys. Furthermore, NAB815 is even less nephrotoxic than NAB739. All animals tolerated it. The heterogeneity in the patient response to polymyxin B and colistin has clinical significance, as some patients appear to be more vulnerable to the nephrotoxic effect than the others. Histopathological comparison of morphologic findings induced by equally high doses (36 mg/kg/d) of NAB739 and NAB815 show less severe nephropathic alterations with NAB815. Accordingly, NAB815 has a clear-cut advantage over NAB739. Whilst not wishing to be bound by theory, this might be due to a difference in the charge distribution. Whereas NAB739 carries all its three positive charges in the heptapeptide ring NAB815 carries only two positive charges in the heptapeptide ring. Thus the heptapeptide ring of NAB815 does not resemble any of the known polymyxins.

In the previous patent application of the same inventors (PCT/FI2007/050441) and publications (Vaara M. et al. 2008. Novel Polymyxin Derivatives Carrying Only Three Positive Charges Are Effective Antibacterial Agents. Antimicrob Agents Chemother 52:3229-3236; Vaara, M., T. Vaara. 2010. Structure-activity studies on novel polymyxin derivatives that carry only three positive charges. Peptides 31:2318-2321), all molecules having two positive charges in the ring portion and one positive charge in the tail portion (NAB715, NAB716, and NAB717), were variations of one theme. The one positive charge in the tail was at R3 location and the two positive charges in the cyclic portion were shifted between three potential locations at R5, R8, and R9. Out of the three combinations (positive charges at R5 & R8, at R5 & R9, and at R8 & R9) only one (R5 & R9) showed activity, which, however, was remarkably lower than that of the best compounds (NAB739 and NAB737) that had all the three positive charges in the cyclic portion (at R5 & R8 & R9).

In designing the compound under the present patent application (NAB815), a totally different approach was taken. In the tail portion, the two hydroxyl groups (due to Thr and DThr at R2 and R3, respectively) were conserved, and the positive charge was placed at R1 (and not at R3). As a surprising result, the high antibacterial activity could was conserved, while one of the three only positive charges was positioned in the tail portion. The earlier patent application and subsequent publications did not disclose any compound having a full-length tail (R1, R2, and R3) with one positive charge in it.

Quite remarkably, as also shown here, NAB815 is excreted into urine in cynomolgus monkeys in a very significant degree while the excretion of polymyxin B is almost absent. This may be advantageous in the therapy of severe infections originating from the urinary tract, such as pyelonephritis caused by Gram-negative bacteria, such as *Escherichia coli*, entering the urinary tract through the urethra and multiplying in the bladder.

Accordingly the present invention provides a compound having formula (I):

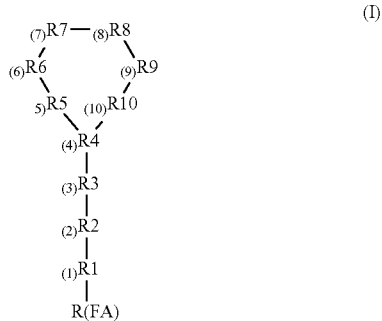

wherein
R1 is Dab
R2 is Thr
R3 is DThr
R4 is Dab
R5 is Dab
R6 is DPhe
R7 is Leu
R8 is Abu
R9 is Dab;
R10 is Thr; and
R(FA) is octanoyl;
and pharmaceutically acceptable salts thereof.

The compound of present invention comprises a cyclic heptapeptide portion R4-R10 and a side chain linked to the N-terminal aminoacyl residue R4. The side chain consist of a R(FA)-tripeptide(R1-R3) residue. R(FA) is an octanoyl residue (OA) linked to the α-amino group of the N-terminal amino acid residue of the tripeptide side chain.

Specifically R1-R10 represents an amino acid sequence Dab-Thr-DThr-cy[Dab-Dab-DPhe-Leu-Abu-Dab-Thr-], i.e. SEQ ID NO. 1. Thus compound according to the present invention is OA- Dab-Thr-DThr-cy[Dab-Dab-DPhe-Leu-Abu-Dab-Thr-], i.e. OA-SEQ ID NO. 1, or a pharmaceutically acceptable salt thereof.

Compounds of formula (I) exhibit high antibacterial activity and show only minor or no undesired nephrotoxic effect on administration as will be shown by exemplary pharmacological test results discussed below.

Abbreviations used herein: Dab refers to α,γ-diamino-n-butyryl i.e. 2,4-diaminobutyryl; Abu refers to 2-aminobutyryl; Thr refers to L-threonine; DThr refers to D-threonine; DPhe refers to D-phenylalanine; Leu refers to L-leucine; and OA refers to octanoyl.

The expression "pharmaceutically acceptable" represents being useful in the preparation a pharmaceutical composition that is generally safe, non-toxic, and neither biologically nor otherwise undesirable, and includes being useful for both veterinary use as well as human pharmaceutical use.

The term "pharmaceutically acceptable salt" refers to salts with acids and bases and which are known to be non-toxic and are commonly used in the pharmaceutical literature. Examples of such salts are acid addition salts formed by the use of pharmaceutically acceptable non-toxic acids such as hydrochloric acid, nitric acid, sulfuric acid, phosphoric acid, oxalic acid, fumaric acid, maleic acid, succinic acid, acetic acid, citric acid, ascorbic acid, maleic acid, benzoic acid, tartaric acid, carbonic acid and the like. A typically used acid for formation of the pharmaceutically acceptable salt is sulfuric acid.

"Comprises" or "comprising" has used herein denotes that the subsequently described set may but need not include other elements.

Compounds of present invention may inhibit growth of or sensitize clinically important Gram-negative bacteria to antibacterial agents. Said Gram-negative bacteria may be those belonging to the genus of *Acinetobacter, Aeromonas, Alcaligenes, Bordetella, Branhamella, Campylobacter, Citrobacter, Enterobacter, Escherichia, Francisella, Fusobacterium, Haemophilus, Helicoibacter, Klebsiella, Legionella, Moraxella, Pasteurella, Plesiomonas, Pseudomonas, Salmonella, Serratia, Shigella,* and *Yersinia* species. The bacteria may be, for example, *Escherichia coli, Klebsiella pneumoniae, Klebsiella oxytoca, Enterobacter cloacae, Enterobacter aerogenes,* other species of *Enterobacter, Citrobacter freundii, Pseudomonas aeruginosa,* other species of *Pseudomonas, Acinetobacter baumannii,* as well as many other species of non-fermentative Gram-negative bacteria. The bacteria also include *Helicobacter pylori,* as well as other clinically important Gram-negative bacteria. In particular the said Gram-negative bacteria are selected from the group consisting of: *Escherichia coli, Klebsiella pneumoniae, Klebsiella oxytoca, Enterobacter cloacae, Citrobacter freundii, Pseudomonas aeruginosa,* and *Acinetobacter baumannii,* preferably said Gram-negative bacteria are selected from the group consisting of: *Escherichia coli, Klebsiella pneumoniae, Pseudomonas aeruginosa,* and *Acinetobacter baumannii*.

The bacterial infections that may be treated with compounds of the present invention include, for example, bacteremia, septicemia, skin and soft tissue infection, pneumonia, meningitis, infections in the pelveoperitoneal region, foreign body infection, fever in hematological patient, infection associated with an intravenous line or other catheter, canyl and/or device, pyelonephritis and other urinary tract infections, infection in gastrointestinal tract, in the eye, or in the ear, superficial skin infection, and colonization of gastrointestinal tract, mucous membranes and/or skin by potentially noxious bacteria.

Compounds of the present invention may be useful for the treatment of bacterial infectious diseases, in particularly those caused by Gram-negative bacterial. Examples of inflammatory diseases and conditions include, but are not limited to, severe hospital-acquired infections, infections of the immunocompromised patients, infections of the organ transplant patients, infections at the intensive care units (ICU), severe infections of burn wounds, severe community-acquired infections, infections of cystic fibrosis patients, as well as infections caused by multi-resistant Gram-negative bacteria.

Accordingly the present invention provides a method of treating an infection caused by Gram-negative bacteria, comprising administering a compound as claimed in claim 1 or 2, or a pharmaceutical composition as claimed in any one of claims 3 to 6, to a patient in need thereof.

Compounds of the present invention may be administered in an effective amount within the daily dosage range of about 1 mg/kg to about 300 mg/kg, preferably between 3 mg/kg to 100 mg/kg body weight. Compounds of the present invention may be administered in a single daily dose, or the total daily dosage may be administered in divided doses of two, three or four times daily.

"An effective amount" refers to an amount of a compound that confers a therapeutic effect on the treated subject. The therapeutic effect may be objective (i.e. measurable by some test or marker) or subjective (i.e. subject gives an indication of or feels an effect). Such treatment need not necessarily completely ameliorate the condition of disease. Further, such treatment or prevention can be used in conjunction with other traditional treatments for reducing the condition known to those skilled in the art.

Compounds of the present invention are most preferably used alone or in other active ingredients, in particular other antibacterial agents. Said other active ingredients may be administered simultaneously or sequentially in any order with the compounds of the present invention. Said antibacterial agents may be selected from the group consisting of clarithromycin, azithromycin, erythromycin and other macrolides, ketolides, fluoroketolides, clindamycin and other lincosamines, streptogramins, rifampin, rifabutin, rifalazil and other rifamycins, fusidic acid, mupirocin, oxazolidinones, vancomycin, dalbavancin, telavancin, oritavancin and other glycopeptide antibiotics, fluoroquinolones, bacitracin, tetracycline and fluorocycline derivatives, betalactam antibiotics, novobiocin, pleuromutilins, folate synthesis inhibitors, deformylase inhibitors, and bacterial efflux pump inhibitors. In particular said antibacterial agents may be selected from the group consisting of: clarithromycin, azithromycin, erythromycin, telithromycin, solithromycin, clindamycin, the streptogramin combination quinupristin-dalfopristin, eravacycline, minocycline, omadacycline, rifampin, rifabutin, rifalazil, fusidic acid, mupirocin, the oxazolidinones tedizolid and linezolid, vancomycin, dalbavancin, oritavancin, telavancin, the fluoroquinolones moxifloxacin, delafloxacin and avarafloxacin, and the folate synthesis inhibitor trimetoprim.

Compounds of the present invention may be administered by various routes, for example, parenteral, subcutaneous, intravenous, intraarticular, intrathecal, intramuscular, intraperitoneal, and by intradermal injections, and via transdermal, rectal, buccal, oromucosal, nasal, ocular routes and via inhalation and via implant.

A pharmaceutical composition comprising a compound of the present invention as an active ingredient may further include pharmaceutically acceptable additives such as pharmaceutically acceptable carrier(s) and/or excipient(s) that facilitate processing of the active compounds into preparations that can be used pharmaceutically. A suitable pharmaceutical composition may comprise a compound of the present invention in combination with one or more other active ingredient(s), in particular an antibacterial agent as discussed above. Compounds may be formulated into a suitable composition; suitable administration forms include, for example, solutions, dispersions, suspensions, powders, capsules, tablets, pills, controlled release capsules, controlled release tablets and controlled release pills.

General Preparation Methods

Compounds of the present invention may be prepared by methods known in the art. The following example illustrates the preparation of a compound of formula (I).

Example 1

Synthesis of NAB815

NAB815, having the structural formula of octanoyl-αDab-Thr-DThr-[cyclo-α,γDab-αDab-DPhe-Leu-Abu-αDab-Thr], where the carboxyterminal Thr at R10 is linked through its carboxyl group to 4-amino group of the 2,4-diaminobutyric acid residue (Dab) at R4, and having the relative molecular mass of 1175.44, can be synthesized for instance by conventional solid phase chemistry using the methodology previously described for other polymyxin derivatives such as NAB739 (U.S. Pat. No. 7,807,637). The amino acid at the C-terminus is commercially available as pre-attached to the solid phase and, when cleaved off the resin with acid, yields a C-terminal carboxylic acid.

The strategy in the protection is to use three levels of orthogonal protection, temporary Fmoc protection for the alpha amino functions, protection of the γ-amino group of the Dab residue involved in cyclization by groups which are removed during the acid cleavage stage, and semi-permanent protection to cover reactive side chain functions while the cyclisation reaction takes place. After cleavage of the peptide from the resin, the C-terminal carboxylic acid is reacted with the γ-amino group of the diaminobutyric acid residue (Dab) at R4 to form a cyclic peptide. After the cyclisation step, the semipermanent protection groups are removed to yield the NAB peptide.

Accordingly, the alpha amino function of the amino acid is protected by a fluorenyl-methoxycarbonyl group (Fmoc) and Fmoc is removed by 20% piperidine in dimethylformamide (DMF) at every cycle. The amino acid that is involved with cyclisation, i.e. Dab at R4, is protected by a tert-butoxycarbonyl group (tBoc), an acid labile group which is removed at the cleavage step. Amino acids which have functional side chain groups are protected by a group that is stable to the acid cleavage stage, i.e. a benzyloxycarbonyl group (Z). Amino acids D-phenylalanine and leucine naturally need no side chain protection. The amino terminus is not protected; this enables direct reaction in the acylation procedure.

The synthesis steps were performed in a commercial automatized synthesizer that employed 0-(6-Chlorobenzotriazol-1-yi)-N,N,N',N'-tetramethyluronium hexafluorophosphate (HCTU) as activator.

The acylation was performed by using a four-fold molar excess of each amino acid or the fatty acid, four-fold molar excess of the activator HCTU (see above), and an eight-fold molar excess of N-methyl morpholine. The reaction time was 30 min.

The amino acids were purchased already protected from standard suppliers. The peptide was removed from the resin by reaction with a solution of 95% trifluoroacetic acid and 5% water for 2 hours at room temperature, to yield the partially protected product. The resulting peptide was precipitated with diethyl ether.

The cyclisation mixture used was benzotriazole-1-yl-oxy-tris-pyrrolidino-phosphonium hexafluorophosphate (PyBop), N-hydroxybenzotri-azole (HoBt), and N-methyl morpholine (NMM) at the molar excess of 2, 2, and 4, respectively. The peptide was dissolved in dimethylformamide, the cyclisation mix was added and allowed to react for 2 hours. The cyclized, protected peptide was precipitated by the addition of cold diethyl ether. Any residual PyBop was removed by washing the peptide with water.

The remaining side chain protection groups (Z) were removed by catalytic dehydrogenation. The peptide was dissolved in acetic acid-methanol-water (5:4:1), under an atmosphere of hydrogen and in the presence of a palladium charcoal catalyst.

The peptide was purified by reverse phase chromatography using conventional gradients of acetonitrile:water:trifluoroacetic acid. The product was dried by lyophilisation.

NAB815 was converted to its sulfate salt. The product was white lyophilisate. Its appearance in solution (1 mg/mL in water) was clear and colourless. When identified by ESI-MS, m was 1175.4 u (average mass).

Pharmacological Tests

The following examples are provided to demonstrate the present invention in illustrative way and should not be considered as limiting in the scope of invention. Further, the concentrations of the compounds in the assays are exemplary and should not be taken as limiting. A person skilled in the art may define pharmaceutically relevant concentrations with methods known in the art. All animal experiments are performed in accordance with standards of ethical conduct and appropriate institutional animal care and use policies.

Example 2

Antibacterial Activity of NAB815 and its Comparators

Source of chemicals: NAB815 sulfate (lot 1051607; purity, 98.8% by HPLC) and NAB739 sulfate having structural formula of octanoyl-Thr-DSer-[cyclo-α,γDab-αDab-DPhe-Leu-αDab-αDab-Thr] i.e. OA-SEQ ID 2 (lot 1049851, purity, 97.3% by HPLC). Polymyxin B sulfate was obtained from Sigma-Aldrich, St. Louis, Mo., USA (catalogue number P0972, lot BCBF8382V; purity, 89.3%).

Minimum inhibitory concentration (MIC) assays were completed in triplicate using CLSI standard methodology and Müller-Hinton II broth as described by Clinical and Laboratory Standards Institute, 2012 (Methods for dilution antimicrobial susceptibility tests for bacteria that grow aerobically. Approved standard, Ninth edition. CLSI document M07-A9. Clinical and Laboratory Standards Institute, Wayne, Pa.) The starting inoculum ($5\times10^5$ CFU/mL) was prepared from overnight cultures on trypticase soy agar containing 5% sheep blood. The microtiter plates were incubated at 35° C. for 20 hours, at which point they were visually read. Synergy studies were performed by using polymyxin derivatives in combination with rifampin, a model compound for such antibacterial agents that the intact outer membrane of Gram-negative bacteria acts as a permeability barrier.

Table 1 shows MIC values (μg/mL) i.e. the antibacterial activity of polymyxin B, a reference compound (NAB739) and a compound according to the present invention (NAB815), alone as well as in combination with a fixed concentration of rifampin (0.25 μg/mL)*; both polymyxin-susceptible and polymyxin-nonsusceptible strains included.

TABLE 1

| Target | Polymyxin B | | Ref. NAB739 | | NAB815 | |
| --- | --- | --- | --- | --- | --- | --- |
| | alone | Rifampin | alone | rifampin | alone | rifampin |
| E. coli ATCC 25922 (8) | 2 | 0.5-1 | 2 | 1 | 2 | 1 |
| E. coli JMI 3328 (8) | 2 | 0.5-1 | 2 | 1 | 4 | 1 |
| K. pneumoniae ATCC 43816 (16) | 2 | 0.5-1 | 4 | 1-2 | 2-4 | 1 |
| K. pneumoniae JMI 27072 (8) | 2 | 1 | 2-4 | 1 | 2-4 | 1-2 |
| A. baumannii ATCC 19606 (4) | 2 | 0.5 | 4 | 0.5 | 4 | 0.5-2 |
| A. baumannii JMI 48125 (4) | 2 | 1 | 2-4 | 0.5 | 2 | 0.5-2 |
| P. aeruginosa ATCC 27853 (32) | 2 | 1 | 8->8 | 4-8 | 16 | >8 |
| P. aeruginosa JMI 7445 (32) | 2 | 1 | 4 | 4 | 8 | 4 |
| E. coli JMI 109 (16) | 4-8 | 0.5-1 | 32 | 1 | 128 | 1 |
| K. pneumoniae JMI 27068 (64) | 64 | 1 | 128 | 2 | 128 | 4 |
| A. baumannii CMI 417 (4) | 32 | 1 | 128 | 2 | 256 | 2 |

* MIC values in the absence of rifampin are a synopsis of modal MIC values from triplicate determinations and of the MICs from duplicate checkerboard assays. MIC values in the presence of rifampin (0.25 μg/mL) are from duplicate checkerboard assays. The modal MICs (μg/mL) of rifampin for each target strain (from triplicate determinations) are shown in parentheses after the name of the target bacterial strain.

The MICs of NAB815 for polymyxin-susceptible strains of E. coli, K. pneumoniae and Acinetobacter were identical or very close to those of NAB739 and polymyxin B. Polymyxin B displayed better activity than NAB815 and NAB739 against Pseudomonas aeruginosa and against two (K. pneumoniae JM109 and A. baumannii CMI417) of the three strains that display decreased susceptibility to polymyxin B.

Sub-inhibitory concentrations of all three peptides remarkably potentiated the activity of rifampin (Table 1). At 1 μg/mL, NAB815 decreased the MIC of rifampin for K. pneumoniae ATCC 43816 from 16 μg/mL to 0.25 μg/mL (i.e. by a factor of 64) and that for E. coli ATCC 25922 and E. coli JM13328 from 8 μg/mL to 0.25 μg/mL (i.e. by a factor of 32). Quite importantly, also the strains that displayed reduced susceptibility to polymyxins were susceptible to the combined activity of NAB815 and rifampin. Very similar results were obtained with NAB739. Against P. aeruginosa, both NAB815 and NAB739 lacked any notable synergistic activity with rifampin.

To conclude, the antibacterial activities of NAB815 and NAB739 were identical or very close to each other, not only alone but also in the presence of rifampin.

Example 3

Toxicity and Toxicokinetic Studies

In vivo toxicity and toxicokinetic studies were performed by using cynomolgus monkeys. The laboratory that performed the animal studies is accredited by the Association for Assessment and Accreditation of Laboratory Animal Care (AAALAC), has an Animal Welfare Assurance issued by the Office of Laboratory Animal Welfare (OLAW), is registered with the United States Department of Agriculture (USDA), and has an Institutional Animal Care and Use Committee (IACUC) responsible for compliance with applicable laws and regulations concerning the humane care and use of laboratory animals.

Naïve female cynomolgus monkeys were acclimatized to study room for 28 days during which each animal was implanted with a permanent indwelling femoral catheter to permit continuous intravenous infusions. The animals were allowed surgical recovery period of at least 2 weeks before initiating dosing.

Source of chemicals was as follows: NAB815 sulfate (lot 1051607; purity 98.8% by HPLC and lot 1054308; purity 98.4% by HPLC) and NAB739 sulfate (lot 1049851, purity 97.3 by HPLC). Polymyxin B sulfate was from Sigma-Aldrich (catalogue number P0972, lot number BCBF8382V). On each day of use, appropriate quantities of NAB739, NAB815 or polymyxin B were weighed and dissolved in appropriate volumes of sterile saline to prepare a stock solution for each test article and positive control. A correction factor was used in the stock solution preparation to account for both the purity and sulfate content in each test article. Accordingly, the dose (such as 36 mg/kg/d) refers to the dose of the pure peptide as its free base form, not as its sulfate salt.

The doses were the following: polymyxin B 18 mg/kg/d (Group 1), polymyxin B 24 mg/kg/d (Group 2), NAB739 24 mg/kg/d (Group 3), NAB739 36 mg/kg/d (Group 4), NAB815 24 mg/kg/d (Group 5), NAB815 36 mg/kg/d (Group 6). Three animals were included in each study groups.

For seven days, the animals were dosed by intravenous (IV) infusion three times daily (TID) at a dose volume of 10 mL/kg for 1 hour (±10 minutes), 8±0.5 hours apart. The day of initial dose administration was designated study Day 1, with subsequent days consecutively numbered. Days prior to the initial dose administration were consecutively numbered with the final day of acclimation referenced as Day −1.

The following parameters were evaluated at designed intervals: clinical observations, body weights, clinical pathology (hematology, coagulation, serum chemistry, urinalysis including urine sediments and urine chemistry), toxicokinetics (plasma and urine) and anatomic pathology (kidney). In cases of animals sacrificed on an unscheduled basis, samples were taken on the day of the sacrifice.

On the day of necropsy, animals were sedated with ketamine, weighed, and anesthetized with an intravenous injection of a commercial pentobarbital and phenytoin solution, followed by exsanguinations.

Terminal necropsy for the surviving animals was conducted on Day 8. Unscheduled necropsy was conducted in the polymyxin B groups on Day 4 for one animal receiving 18 mg/kg/d (Group 1) and for two animals receiving 24 mg/kg/d (Group 2), and on Day 5 for two animals receiving 18 mg/kg/d (Group 1). Unscheduled necropsy was also conducted on Day 5 for one animal in the NAB739 group receiving 36 mg/kg/d (Group 4).

At necropsy, gross observations and organ weights were recorded, and specific tissues were collected. Histopathology was conducted on sections of kidney stained with hematoxylin and eosin (H&E).

Plasma and urine concentrations for toxicokinetic (TK) studies were determined by using liquid chromatograph interfaced with a mass spectrometer after precipitation of proteins. A sample (100 µL) was mixed with internal standard solution in water:formic acid (99:1 v/v; 50 mL). Then, 600 µL of 100:1 acetonitrile:formic acid was added. The plates were centrifuged at 3200 rpm for 5 minutes. Using a Tomtec Quadra96, a 450 µL aliquot was transferred to a new 96-well plate and dried under nitrogen at 40° C. Then, 200 µL of water:methanol:formic acid (85:15:1 1 v/v) was added and the plate sealed for LC-MS/MS injection. LC-MS system consisted of Waters Acquity liquid chromatograph interfaced with a Thermo Scientific TSQ Quantitative triple quadrupole MS with ionization in the positive ion mode. Each sample (20 µL) was injected onto a Waters Acquity BEH Shield RP18 column (2.1×50 mm; 1.7 µm) equilibrated at 50° C. Mobile Phase A was 85:15:1 v/v water:methanol:formic acid. Mobile Phase B was 50:50:1 v/v acetonitrile:methanol:formic acid.

The gradient that was suitable for quantifying all the compounds is shown in Table 2.

TABLE 2

| Time (min) | Flow Rate (mL/min) | % A | B |
|---|---|---|---|
| 0.00 | 0.400 | 100.0 | 0.0 |
| 1.00 | 0.400 | 100.0 | 0.0 |
| 1.10 | 0.400 | 88.0 | 2.0 |
| 3.00 | 0.400 | 88.0 | 2.0 |
| 3.10 | 0.400 | 84.0 | 6.0 |
| 6.00 | 0.400 | 84.0 | 6.0 |
| 6.10 | 0.400 | 50.0 | 0.0 |
| 7.90 | 0.400 | 50.0 | 0.0 |
| 8.00 | 0.400 | 100.0 | 0.0 |
| 10.0 | 0.400 | 100.0 | 0.0 |

The mass transitions and retention times for each compound were are shown in Table 3.

TABLE 3

| Compound | Retention Time | Q1 m/z | Q3 m/z |
|---|---|---|---|
| Polymyxin B | 2.97 | 602.67 | 101.123 |
| NAB739 | 5.08 | 539.11 | 120.77 |
| NAB815 | 5.32 | 588.67 | 101.121 |
| Colistin | 2.78 | 585.67 | 86.206 |

Peak area ratios from the calibration standard responses were regressed using a (1/concentration$^2$) linear fit for polymyxin B using colistin as the internal standard. For NAB739 and NAB815, peak areas from the calibration standard responses were regressed using a (1/concentration$^2$) quadratic fit (without the use of an internal standard).

The regression models were chosen based upon the behavior of the analytes across the concentration range used during development.

Toxicokinetic analysis was performed by using WinNonlin Phoenix version 6.3 software (Pharsight, Cary, N.C.). For plasma TK, noncompartmental IV infusion model was used.

Figure 2:
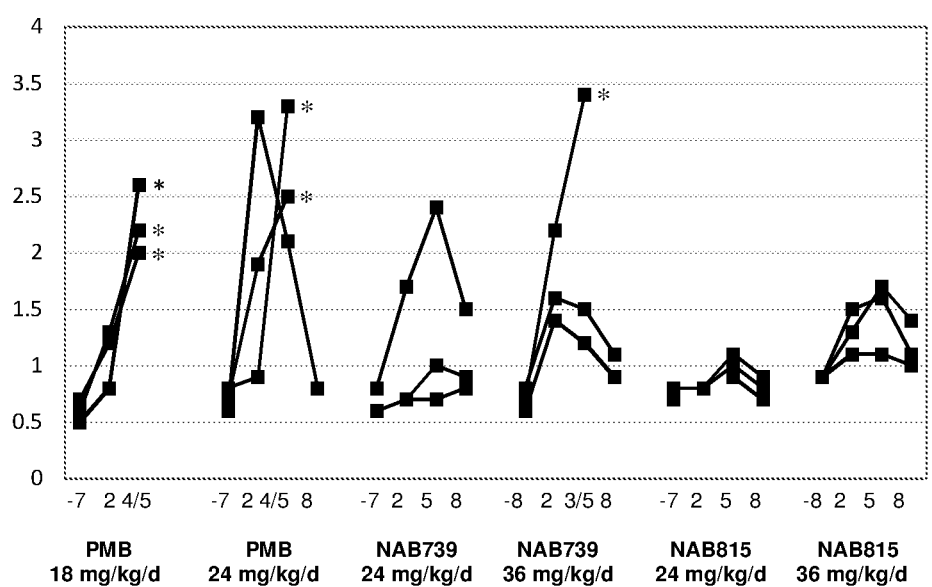
FIG. 2 shows S-Crea (mg/dL) before (day −7/−8) and during (days 2-8) treatment with polymyxin B (PMB), NAB739, or NAB815 (3 animals per group, IV, TID)
Figure 3:
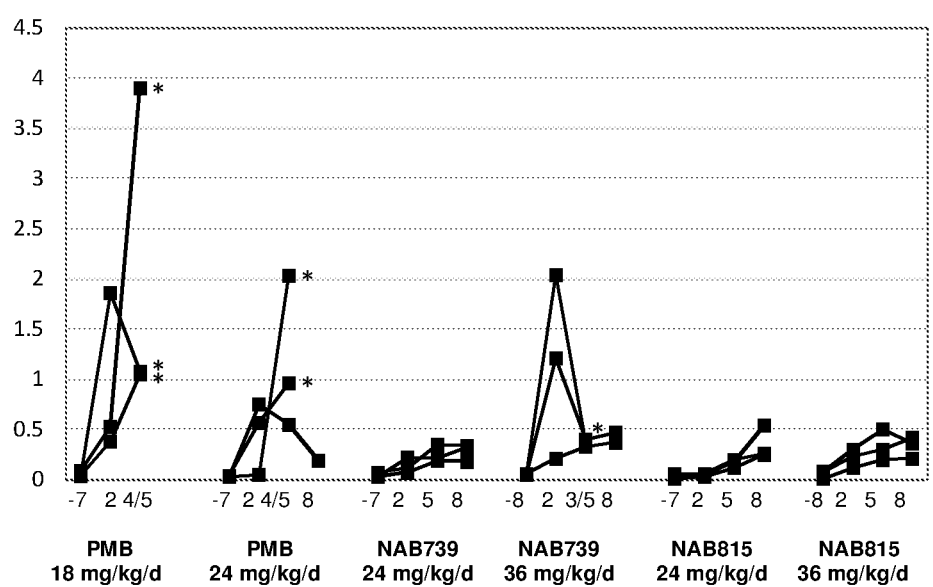
FIG. 3 shows U-NAG (U/L)/U-Crea (mg/dL) ratio×10 before (day −7/−8) and during (days 2-8) treatment with polymyxin B (PMB), NAB739, or NAB815 (3 animals per group, IV, TID)
Figure 4:
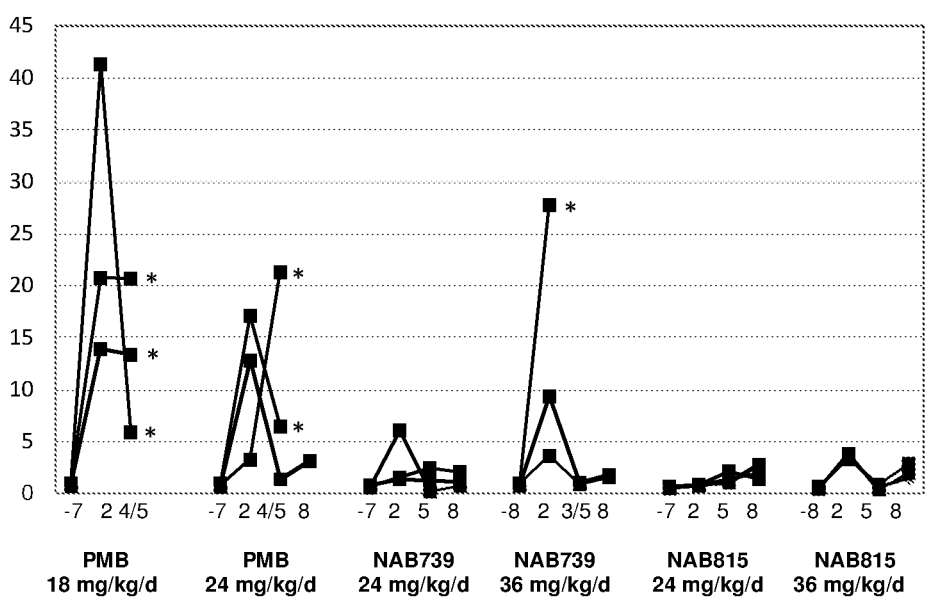
FIG. 4 shows U-GGT (U/L)/U-Crea (mg/dL) ratio before (day −7/−8) and during (days 2-8) treatment with polymyxin B (PMB), NAB739, or NAB815 (3 animals per group, IV, TID).

Figures shows levels of Blood Urea Nitrogen (S-BUN; FIG. 1) and Blood Creatinine (S-Crea; FIG. 2), both blood markers for kidney injury, in the animals before the treatment and in the same animals subsequently receiving polymyxin B, NAB739 or NAB815. The figures also show Urine N-acetyl-β-D-glucosaminidase/urine creatinine ratio (U-NAG/Crea; FIG. 3) and Urine Gamma Glutamyltransferase/urine creatinine ratio (U-GGT/Crea; FIG. 4), both urine biomarkers for kidney injury, in those animals. S-Crea and U-Crea were measured by using an Olympus Analyzer (OA) and the modified Jaffe method, S-BUN by using OA and urease/L-glutamate dehydrogenase. U-NAG was measured by using OA/enzymatic, and U-GGT by using OA and glutamyl-carboxy-p-nitroanilide IFCC. In the FIGS. 1 to 4 "*" indicates that the animal had to be euthanized due to severe nephrotoxic effects.

It can be concluded that NAB815 was significantly better tolerated than NAB739. One animal receiving NAB739 at 36 mg/kg/d had to be euthanized due to severe nephrotoxic effects. In this animal, all the four markers were significantly elevated. In another animal receiving NAB739 at 36 mg/kg/d both urine biomarkers were remarkably elevated. In contrast, the NAB815 animals displayed only minor if any elevations in the four parameters, and underwent no pre-scheduled necropsy.

At the dose of 24 mg/kg/d, one animal receiving NAB739 displayed marked increase in S-Crea. None of the parameters was elevated in the animals receiving an equivalent dose of NAB815.

As expected, polymyxin B was markedly toxic. Two animals receiving polymyxin B at 24 mg/kg/d and all the three animals receiving polymyxin B at 18 mg/kg/d had to be euthanized. In all the six animals, S-BUN, S-Crea and U-GGT/Crea were remarkably increased. U-NAG/Crea was remarkably increased in five of the animals.

Histopathological comparison of morphologic findings induced by equally high doses (36 mg/kg/d) of NAB739 and NAB815 showed less severe nephropathic alterations with NAB815. The presence of the following nephro-pathological parameters was recorded in each animal: tubular basophilia (re-generation), tubular degeneration/necrosis, infiltration (by mononuclear and/or mixed inflammatory cells), tubular dilatation, and tubular casts. Each parameter was scored as follows: Grade Code=0: no significant findings; 1: minimal; 2: mild; 3: moderate; 4: marked. Marked findings were recorded in the euthanized NAB739-treated animal only, and were the following: marked tubular degeneration/necrosis as well as marked presence of tubular casts. The NAB739-treated animals that survived the treatment had moderate findings, both in two parameters. Two of the NAB815-treated animals had moderate findings, both in one parameter only. The third NAB815-treated animal had no other than minimal or mild findings. Accordingly, the NAB815-treated animals had less severe tissue alterations relative to those observed in the NAB739-treated animals.

Area under the concentration-time from time 0 h to 8 h (AUCs 0-8 h, hr*μg/mL) of NAB815 after the infusion of 8 mg/kg was 102 (SD=5), when determined on day 1, and 110 (SD=12), when determined on day 7. After the equivalent dose (8 mg/kg) of NAB739 the corresponding values were 108 (SD=2) and 137 (SD=2). After the equivalent dose of polymyxin B (8 mg/mL) the value was 112 (SD=5), when determined on day 1. Accordingly, the AUC values for each three compounds were very close to each other.

Quite remarkably, a very significant portion of the dose of NAB815 was excreted into urine within 8 hours after the infusion (0-8 h recovery). After the infusion of 8 mg/kg of NAB815, the 0-8 h recovery was up to 38%, 55%, and 88% of the dose (percentages given for each animal). The corresponding recovery rates for NAB739 were up to 20%, 91%, and 92% and those for polymyxin B 1%, 2%, and 2%. The resulting concentrations of NAB815 and NAB739 in the urine were very high. After the infusion of NAB815 at 8 mg/kg, concentrations as high as 175, 225, and 260 g/mL were found either in the 0-4 h or 4-8 h sample (concentrations given for each animal). The corresponding concentrations for NAB739 were 80, 140, and 155 g/mL and those for polymyxin B 7, 9, and 15 μg/mL.

Example 4

Further Pharmacokinetic Data

In the cynomolgus monkey studies described in Example 3, where the peptides were administered as a 1-hour intravenous infusion three times daily, plasma and urine levels of the peptides were determined.

When the peptides were dosed at 36 mg/kg/d, the AUCs (hr*μg/ml) of NAB815 were 153 (SD=32) and 205 (SD=56) on days 1 and 7, respectively. The corresponding values for NAB739 were 239 (SD=9) and 302 (no SD, only two animals). At this dosage, the urinary recoveries (0-8 h urine collection) of NAB815 were 14.3%, 20.9%, and 36.3% for the three animals on day 1 and 33.9%, 40.5%, and 41.9% on day 7, respectively. The corresponding values for NAB739 were 15.4%, 20.4%, and 26.4% on day 1 and 30.6% and 55.8% on day 7 (only two animals). Furthermore, the urine concentrations (μg/ml, in 0-8 h urine collection) of NAB815 were 114, 173, and 265 for the three animals on day 1, and 17, 62, and 149 on day 7, respectfully. The corresponding values for NAB739 were 33, 82, and 92 on day 1 and 268 and 348 on day 7 (only two animals).

Example 5

Comparative Efficacy of NAB815 and Polymyxin B in Murine Urinary Tract Infection The study used 64 outbred, OF-1 female mice (Charles River, France) weighing 28-32 grams and *Escherichia coli* C175-94 (serotype O8:K48:H4), a clinical isolate elaborating type 1 fimbriae. The peptides were NAB815 (Lot 1054308) and polymyxin B (Sigma-Aldrich, batch BCBF8382V). The study was performed by Statens Serum Institut, Copenhagen, Denmark.

Three days before the start of the study and during the study, the mice had free access to 5% glucose in drinking water.

On day 0, the urine was removed from the bladder by gently pressing the abdomen. Thereafter, the mouse was anaesthetized with approximately 0.15 ml of Zoletil mix s.c. A syringe with polyethylene catheter (Becton Dickison) containing the bacterial suspension was inserted via the urethra into the bladder and 50 μl of the bacterial inoculum was slowly injected into the bladder. Thereafter, the mouse was left in the cage. Mice were kept in a warming cabinet and were under surveillance until fully awake.

After measuring the colony forming units (CFUs), the inoculum was determined to contain 9.38 log 10 CFU/ml, corresponding to 8.08 log 10 CFU/mouse.

On day 1 and day 2 postinfection, the mice were treated subcutaneously with solutions (0.2 ml) containing NAB815, polymyxin B or vehicle (0.9% NaCl) twice a day. The treatment groups (six mice in each) were the following: vehicle control; NAB815, 0.25 mg/kg/dose; NAB815, 0.5 mg/kg/dose; NAB815, 1 mg/kg/dose; NAB815, 2 mg/kg/dose; polymyxin B, 0.25 mg/kg/dose; polymyxin B, 0.5 mg/kg/dose; polymyxin B, 1 mg/kg/dose; and polymyxin B, 2 mg/kg/dose. In addition, one group served as a pretreatment control to help to assess as how the infection has proceeded before the start of the treatment on day 1 postinfection.

On days 1, 2 and 3 postinfection urine was sampled for colony counts. On day 1 postinfection (pretreatment control group) and on day 3 postinfection (all the other groups) after the urine sample was taken, mice were sacrificed by cervical dislocation and bladder and kidneys were removed aseptically. The bladder and kidneys were stored at −80° C. and later homogenized in 0.5 and 1 ml saline, respectively.

CFUs in urine were determined immediately within 2-3 hours after sampling. Frozen organs were thawed and homogenized with steel beads on a tissue lyser. All samples, urine, kidney and bladder, were 10 fold diluted in saline and 20-μl spots were applied on blood agar plates in duplicates. In addition, undiluted samples of urine (2-100 μl depending on the amount of urine) were spread on a separate agar plate to determine the lowest possible detection level of the colony counts. All agar plates were incubated 18-22 h at 35° C. in ambient air.

Treatment with 1 and 2 mg/kg/dose NAB815 resulted in significant reduction of CFU levels in urine, when the levels in the pretreatment control group on day 1 postinfection were compared with the levels two days after the start of the treatment on day 3 (** $p<0.01$ and * $p<0.05$, respectively (ANNOVA Dunnett's multiple comparison test)). In contrast, no significant differences between the corresponding levels were found in the vehicle control group, in the NAB815 groups receiving 0.25 and 0.5 mg/kg/dose and in any polymyxin B groups.

Treatment with NAB815 showed a tendency of a dose-response in the CFUs in the bladder and in the kidneys whereas the treatment with polymyxin B did not show any dose-response tendency.

Of all the 24 mice treated with NAB815 at 0.25-2 mg/kg/dose, bacterial levels were below the detection limit in the urine of 8 mice and in the kidneys of 20 mice, whereas the corresponding numbers of mice treated with polymyxin B were 1 and 10, respectively.

NAB815 is unequivocally more efficient in the treatment of urinary tract infection than polymyxin B.

In conclusion, NAB815 was significantly less nephrotoxic than NAB739. The AUC for both compounds were very close to each other. Both were excreted in urine in a very significant degree, resulting in very high concentrations in urine.

It will be known to a person skilled in the art that, as the technology advances, the inventive concept can be implemented in various ways. The invention and its embodiments are not limited to the examples described above but may vary within the scope of the claims.

The invention claimed is:

1. A compound of the general formula (I),

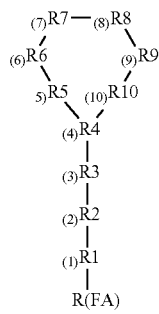

wherein:
R1 is Dab;
R2 is Thr;
R3 is DThr;
R4 is Dab;
R5 is Dab;
R6 is DPhe
R7 is Leu;
R8 is Abu;
R9 is Dab;
R10 is Thr; and
R(FA) is octanoyl;
or a pharmaceutically acceptable salt thereof.

2. A pharmaceutical composition comprising an effective amount of a compound or a pharmaceutically acceptable salt thereof as claimed in claim 1 and at least one pharmaceutically acceptable carrier and/or excipient.

3. A pharmaceutical composition as claimed in claim 2, further comprising one or more other antibacterial agents.

4. A pharmaceutical composition as claimed in claim 3, wherein the one or more other antibacterial agents are selected from the group consisting of clarithromycin, azithromycin, erythromycin and other macrolides, ketolides, fluoroketolides, clindamycin and other lincosamines, streptogramins, rifampin, rifabutin, rifalazil and other rifamycins, fusidic acid, mupirocin, oxazolidinones, vancomycin, dalbavancin, telavancin, oritavancin and other glycopeptide antibiotics, fluoroquinolones, bacitracin, tetracycline and fluorocycline derivatives, betalactam antibiotics, novobiocin, pleuromutilins, folate synthesis inhibitors, deformylase inhibitors, and bacterial efflux pump inhibitors.

5. A pharmaceutical composition as claimed in claim 4, wherein the one or more other antibacterial agents are selected from the group consisting of: clarithromycin, azithromycin, erythromycin, telithromycin, solithromycin, clindamycin, the streptogramin combination quinupristin-dalfopristin, eravacycline, minocycline, omadacycline, rifampin, rifabutin, rifalazil, fusidic acid, mupirocin, the oxazolidinones tedizolid and linezolid, vancomycin, dalbavancin, oritavancin, telavancin, the fluoroquinolones moxifloxacin, delafloxacin and avarafloxacin, and the folate synthesis inhibitor trimetoprim.

6. A method of treating a bacterial infection in a subject in need thereof comprising administering to the subject a therapeutically effective amount of the compound of claim 1, wherein the bacterial infection is caused by a Gram negative bacteria.

7. The method of claim 6, wherein the compound further comprises at least one pharmaceutically acceptable carrier and/or excipient.

8. The method of claim 6, wherein the compound further comprises one or more other antibacterial agents.

9. The method of claim 8, wherein the one or more other antibacterial agents are selected from the group consisting of: clarithromycin, azithromycin, erythromycin and other macrolides, ketolides, fluoroketolides, clindamycin and other lincosamines, streptogramins, rifampin, rifabutin, rifalazil and other rifamycins, fusidic acid, mupirocin, oxazolidinones, vancomycin, dalbavancin, telavancin, oritavancin and other glycopeptide antibiotics, fluoroquinolones, bacitracin, tetracycline and fluorocycline derivatives, betalactam antibiotics, novobiocin, pleuromutilins, folate synthesis inhibitors, deformylase inhibitors, and bacterial efflux pump inhibitors.

10. The method of claim 9, wherein the one or more other antibacterial agents are selected from the group consisting of: clarithromycin, azithromycin, erythromycin, telithromycin, solithromycin, clindamycin, the streptogramin combination quinupristin-dalfopristin, eravacycline, minocycline, omadacycline, rifampin, rifabutin, rifalazil, fusidic acid, mupirocin, the oxazolidinones tedizolid and linezolid, vancomycin, dalbavancin, oritavancin, televancin, the fluoroquinolones moxifloxacin, delafloxacin and avarafloxacin, and the folate synthesis inhibitor trimetoprim.

11. The method of claim 6, wherein the bacterial infection is caused a bacteria selected from the group consisting of: *Escherichia coli, Klebsiella pneumoniae, Klebsiella oxytoca, Enterobacter cloacae, Citrobacter freundii, Pseudomonas aeruginosa*, and *Acinetobacter baumannii*.

12. The method of claim 6, wherein the bacterial infection is a urinary tract infection.

* * * * *